United States Patent [19]

Hibi

[11] Patent Number: 5,612,077
[45] Date of Patent: Mar. 18, 1997

[54] METHOD OF PROCESSING GARLIC AND PREPARING AJOENE-CONTAINING EDIBLE OIL PRODUCTS

[75] Inventor: Takayoshi Hibi, Nagoya, Japan

[73] Assignee: Nagoyaseiraku Co., Ltd., Aichi-Ken, Japan

[21] Appl. No.: 446,327

[22] Filed: May 22, 1995

[30] Foreign Application Priority Data

Sep. 16, 1994 [JP] Japan ................................... 6-221937

[51] Int. Cl.$^6$ ..................................................... A23L 1/22
[52] U.S. Cl. .......................... 426/533; 426/615; 426/638; 426/425; 426/489; 426/506
[58] Field of Search ............................. 426/49, 533, 615, 426/541, 544, 638, 648, 655, 422, 425, 478, 489, 506

[56] References Cited

U.S. PATENT DOCUMENTS 4,665,088  5/1987  Apitz-Castro et al. .

FOREIGN PATENT DOCUMENTS 0232501    8/1987  European Pat. Off. .
62-129224  6/1987  Japan .

OTHER PUBLICATIONS

Lawson et al., Dialog (R) File 07993948 92131948 abstracting Planta Med, Aug. 1991, 57(4), pp. 363–370.
Journal of American Chemical Society 106, pp. 8295–8296, by Eric Block et a., 1984.
Biochemical and Biophysical Research Communications, pp. 145–150, by Rafael Apitz–Castro et al., Nov. 26, 1986.
Applied and Environmental Microbiology, pp. 615–617, by Susumu Yoshida et al., Mar. 1987.
Cancer Letters 53, pp. 103–108 by K. Scharfenberg et a., 1990.
Anticancer Research 11, pp. 2037–2042, by Padma P. Tadi et al., 1991.
Planta Medica 57, pp. 363–370, by Larry D. Lawson, 1991.
AIDS vol. 6 No. 10, pp. 1215–1217, by A. V. Tatarintsev et al., 1992.
Planta Medica 58, pp. 417–423, by Norbert D. Weber et al., 1992.
Journal of the American Chemical Society, vol. 106, No. 26, Dec. 26, 1984.
Journal of the American Chemical Society, vol. 108, No. 22, Oct. 29, 1986.
JP–A–62 129224, vol. 11, No. 357, Nov. 20, 1987, "Processing of Garlic", p. 1–Abstract.
JP–A–63 008328, vol. 12, No. 209, Jun. 15, 1988, "Remedy for Liver Disease", p. 1–Abstract.
Chemical Abstracts, vol. 109, No. 2, Jul. 11, 1988, Abstract No. 11719m, p. 35.
DeSilver, D., Garlic: a Pungent, Powerful herb. Vegetarian Times, n 143, p. 56 (4) Jul., 1989, from Dialog (R) File 149:IAC (SM) Health & Wellness.

*Primary Examiner*—Leslie Wong
*Attorney, Agent, or Firm*—Davis and Bujold

[57] ABSTRACT

The method of processing garlic for efficiently forming Z-ajoene is provided. In the method, 100 parts by weight of water is added to 100 parts by weight of garlic bulbs, the garlic is mashed and the mashed garlic, or the juice extracted therefrom, is brought into contact with edible oil. The pH value of mashed garlic, or the juice extracted therefrom, is approximately adjusted to neutral, or between about 6 and 8. After edible oil is added to and mixed with garlic, or the juice extracted therefrom, the mixture is incubated between 0° C. and 50° C., and Z-ajoene is formed in oil.

5 Claims, No Drawings

METHOD OF PROCESSING GARLIC AND PREPARING AJOENE-CONTAINING EDIBLE OIL PRODUCTS

FIELD OF THE INVENTION

This invention relates to a method of preparing ajoene-containing edible oil products. In particular, a method for efficiently extracting bio-active substances from garlic, especially Z-ajoene by contacting mashed garlic with edible oils under specific conditions.

BACKGROUND OF THE INVENTION

Garlic is a bulbous plant belonging to the genus Allium, and is a very popular seasoning. Garlic has also been used as a folk medicine for diseases such as arteriosclerosis, pulmonary tuberculosis and bronchitis, and as an antimicrobial agent and vermicide. It is believed that the major causal substances providing these medicinal effects of garlic are allicin, ajoene and other sulfur-containing organic compounds. Block et al. (J. American Chem. Soc. 106, P8295–8296, 1984) reported that ajoene, one of the sulfur-containing medicinal substances obtained from garlic, inhibits platelet aggregation and is prepared by incubating chopped garlic in methyl alcohol.

The mechanism of the platelet aggregation inhibition of ajoene was studied by Apitz-Castro et al., and it is expected that ajoene will be a potent preventive and curing agent of thrombosis, arteriosclerosis, hyperlipemia or other circulatory diseases. Tadi et al. reported that ajoene inhibits the interaction between aflatoxin $B_1$ (one of the strongest known carcinogens) and DNA. Scharfenberg et al. also found that ajoene has cytotoxic effect on tumor cells. Furthermore, the anti-eumycetes and antifungal actions of ajoene were reported by Yoshida et al. Its antiviral effects were reported by Weber et al. and some anti-AIDS effects were reported by Tatarintsev et al. Ajoene provides the same degree of antibacterial and antifungal effect as 5-fluorocytosine, and is expected as an antibacterial and antifungal agent.

Ajoene, having the aforementioned strong effects, is not found in natural garlic. It is known that ajoene is formed by polymerization of decomposed products of allicin, which is formed by enzymatic decomposition of alliin (sulfur-containing substance) with aliinase, under some specific conditions.

Lawson et al. (Planta Medica 57, P363–370, 1991) investigated many garlic health foods in the world and reported that he found ajoene only in vegetable oil macerated garlic products. However, the ajoene content he reported is as little as 60 to 148 µg/g product, and the content of Z-ajoene having a strong bio-activity in the total ajoenes is only 50% or less.

Regarding the method of preparing ajoene, it is disclosed in Japanese Laid-open Patent Application No. 62-129224 that when garlic is heated to 40°–90° C. in ethyl alcohol, methyl alcohol or other organic solvent having an acidity of pH 2–6 ajoene is obtained.

In the processing method using the aforementioned organic solvent, only a slight amount, about 900 µg of ajoene per 1 kg of garlic is obtained. To obtain the necessary amount of ajoene, a large amount of garlic is required. When ajoene is produced with such a processing method for utilization in foods and drugs, some processes such as the removal of solvent, refinement and so on, complicate the process steps of the method. Moreover, in the above-mentioned method, only a small amount of Z-ajoene, that has a strong bio-activity on inhibition of platelet aggregation and antibacterial and antifungal activities, is obtained.

SUMMARY OF THE INVENTION

The object of the present invention is to provide a method of processing garlic by mixing mashed garlic with an edible oil for efficient preparation of strongly bio-active Z-ajoene in the oil.

This or other object(s) is attained by a method of processing garlic according to the invention. In the present method, 0 to 100 parts by weight of water is added to 100 parts by weight of garlic bulbs, and the garlic bulbs are mashed. Edible oil is added to and mixed with the mashed garlic. The mixture is incubated at a temperature ranging between 0° C. and 55° C., for a period of three hours to seven days. Thus, ajoene is formed and accumulated in the oil.

In a method of processing garlic according to another aspect of the invention, 0 to 100 parts by weight of water is added to 100 parts by weight of garlic bulbs, and the garlic bulbs are mashed. Garlic juice is separated from the mashed mixture by filtration, and the pH value of the garlic juice is adjusted to between 5.5 and 8.5. Edible oil is then added and mixed with the garlic juice. The mixture is incubated at a temperature ranging between 0° C. and 55° C. for a period of three hours to seven days. Thus, ajoene is formed with more efficiency and accumulated in the oil.

In the aforementioned methods of processing garlic, the amount of water to be added to 100 parts by weight of garlic bulbs is preferably 0 to 50 parts by weight.

In the aforementioned methods of processing garlic, the temperature range in which the mixture of the mashed garlic or garlic juice and edible oil is incubated is preferably between 0° C. and 50° C.

In the aforementioned methods of processing garlic, the oil used is preferably a medium-chain fatty acid triglyceride, because the oil increases the yield of ajoene.

In the aforementioned methods of processing garlic, 300 mg or more ajoene can be formed from 1 kg of raw garlic bulbs, and the molecular ratio of Z-ajoene to E-ajoene or Z/E ratio in the formed ajoene is preferably at least 4.

In the invention, ajoene-containing edible oil is prepared in the aforementioned methods of processing garlic under the aforementioned conditions.

DETAILED DESCRIPTION OF PREFERRED EMBODIMENTS

The embodiments of this invention are now explained together with reference examples. The invention, however, is not limited to the disclosed embodiments.

The raw garlic for use in the invention is preferably bulbs from one of the varieties of garlic belonging to Allium sativum L. Raw material, garlic bulbs containing a sufficient amount of the essential component, alliin and alliinase, (EC 4.4.1.4.) can be used, whether they are raw garlic bulbs, low-temperature stored bulbs or dried bulbs.

Ajoene referred to in the invention (E,Z)-4,5,9-trithia-dodeca-1,6,11-triene-9-oxide having the structural formula:

CHEMICAL FORMULA 1

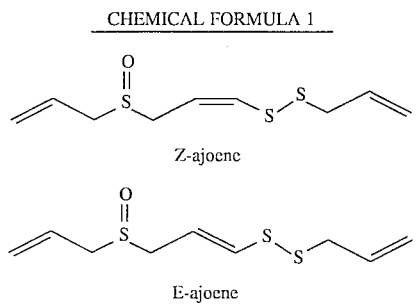

Z-ajoene

E-ajoene wherein ajoene is formed by polymerization of decomposed substances of allicin. The geometrical isomers of E-ajoene and Z-ajoene are present. Block et al. reported that Z-ajoene has an inhibition activity of platelet aggregation that is about 1.3 times stronger as compared with E-ajoene.

In the invention, the garlic may be mashed by grinding, fine-cutting or other suitable method. In order to obtain a relatively large amount of ajoene, it is only required that the garlic bulbs are finely pulverized, such that, after addition of a suitable quantity of water, the amount of garlic juice is increased, and oil-soluble substances including ajoene will be easily extracted. The means for mashing garlic bulbs is not especially specified: food processors, homogenizers or other suitable means can be used.

In order to decrease the amount of edible oil consumed in the process and to increase the concentration of ajoene or other suitable in the oil phase, the amount of water to be added to garlic bulbs is preferably equivalent to or less than the total weight of the garlic bulbs. Such effect can be increased further, for example, by adjusting the amount of water added to the garlic bulbs to the half the total weight of the garlic bulbs or less.

When the mashed garlic is mixed with oil, an appreciable yield of ajoene is obtained. However, when the juice is mixed with oil after squeezing juice from the mashed garlic, the subsequent process steps can be easily carried out and a better yield of ajoene is obtained. The method of juicing the mashed garlic is not specified: juicers, hydraulic presses or other suitable means can be used.

The pH value of garlic juice is usually about 6.6, which is regarded as neutral. For increasing ajoene formation and increasing the Z/E ratio, it is preferably between 5.5 and 8.5 and, more preferably, between 6 and 8. The pH value of garlic juice is usually about 6.6, regarded as neutral, which requires no pH adjustment. When typical garlic bulbs are used, no addition of pyridoxine or other coenzyme is required.

When ajoene is formed by mixing the mashed garlic or garlic juice with edible oil, the type of edible oil or fat is not specified. The type of edible oil that is best mixed with the mashed garlic depends on the application and the desired form of ajoene or ajoene-containing oil, i.e. whether it is used in a food or a drug. It is known that alcohols, ketones or other organic solvents can be used for preparing ajoene, but only a relatively small amount of ajoene can be gained in this manner. In view of wholesomeness, the use of edible oil is more appropriate for health foods.

Edible oils used in this invention can be vegetable oil, animal oil or fat, hydrogenated vegetable oil or animal fat, fractionated oil or fat, interesterified oil or fat, or synthetic oil or fat. When a medium-chain fatty acid triglyceride (referred to as MCT hereinunder) is used, a relatively large amount of ajoene is obtained. In the invention MCT means a triglyceride whose major components are capric acid, caprylic acid, caproic acid and lauric acid.

By sufficiently mixing, the mashed garlic or garlic juice is efficiently contacted with the edible oil. Liquid oil is preferably used in the invention. When a fat having a high melting point is used, the temperature at which it is mixed with the mashed garlic or garlic juice and incubated must be raised above the melting point of the fat. The suitable temperature range for incubating the mashed garlic or garlic juice, while it is in contact with oil or fat, is between the freezing point of the mashed garlic and 55° C. The amount of ajoene will reach its maximum value in a relatively long time period at low temperatures, while it will reach its maximum value in a relatively short time period at high temperatures.

The optimum time period it takes the amount of ajoene to reach its maximum value is in inverse proportion to the incubating temperature. It takes at least seven days at 4° C., one to three days at 20° C., six to 24 hours at 37° C., and three to 24 hours at 50° C. When the incubating temperature exceeds 55° C., the rate of ajoene formation is increased, however, the maximum ajoene level is decreased, and furthermore that the maximum ajoene level decreases faster with the lapse of time. Therefore, when the incubating temperature exceeds 55° C., the control of the incubating and cooling temperatures becomes unfavorably intricate. When the incubating temperature is below 55° C., at least 300 mg of ajoene is obtained in the oil from 1 kg of raw garlic. Moreover, the ratio of geometrical isomers of ajoene (Z/E ratio) is at least 4. In the invention, the most preferable incubating temperature is therefore below 50° C.

In the method of processing garlic according to the invention, a large amount of ajoene can be stably obtained. Since the oil-soluble components are sufficiently recovered from the mashed garlic, an excellent oily product is obtained.

When the appropriate conditions are selected, the content of ajoene reaches 500 to 700 µg per 1 g of product, and the Z/E ratio reaches over 4. The amount of ajoene formed with the method according to the invention is about 330 times as large as that resulting from the known method using ethyl alcohol. The platelet aggregation inhibiting effect, which is calculated in terms of the Z-ajoene content, of the invention is about 370 times as large as that of the known method. The ajoene content in the products prepared according to the invention is about 3.4 to 11.6 times as large as that in the health foods reported by Lawson et al. The platelet aggregation inhibiting action of the invention is about 3.8 to 13 times as large as that of the products reported by Lawson et al.

DETERMINATION OF AJOENE

Ajoene was determined in the following method: 10 ml of the reacted upper oil layer was centrifuged at 5000 rpm for ten minutes, 2.5 g of supernatant was taken, the volume of solution was adjusted to 25 ml by adding dichloromethane to the solution, then, the solution was filtered using a 0.2 µm polytetrafluoroethylene filter manufactured by Toyo Roshi Co., Ltd. to prepare a sample solution. A standard ajoene solution was also prepared with dichloromethane in the same manner, and the two prepared solutions were analyzed using high performance liquid chromatography (HPLC).

The measuring conditions were as follows:

separation column, SUPELCOSIL LC-Si having dimensions of 4.6 mm(inner diameter)×250 mm, manufactured by Supelco Japan Co., Ltd.;

guard column, SUPELCOSIL LC-Si having dimensions of 4.4 mm(inner diameter)×33 mm, manufactured by Supelco Japan Co., Ltd.;

eluent, hexane:isopropanol=95:5 (V/V);

flow rate, 2 ml/min.; and detection wave length, 240 nm.

FIRST EMBODIMENT, FIRST REFERENCE EXAMPLE

INFLUENCE OF pH VALUE 330 g of water was added to 1.1 kg of raw garlic bulbs of a variety called "White Six Pieces", that was produced in Aomori prefecture in Japan. In this and other embodiments and reference examples, the same variety of garlic was used. Subsequently, the garlic and water was mashed using the DLC-X PLUS food processor manufactured by Cuisinart Co., and was manually squeezed using a nylon filtering cloth, such that 800 g of juice was obtained. The juice was divided into eleven equal portions and 80 g samples were taken from each of the portions. The respective pH values of the first six samples were adjusted to 2, 3, 4, 5, 5.5 and 6 with citric acid, and those of the next four samples were adjusted to 8, 8.5, 9 and 10 with sodium hydroxide. The pH value of the eleventh sample, whose pH value was not adjusted, was 6.57. Into each of the eleven samples, 80 g of MCT ("Panacate 810" Nihon Oil and Fat Co., Ltd.) was added and mixed using a type M homogenizing mixer (Tokushu Kika Kogyo Co., Ltd.). The mixtures were incubated at 37° C. for 24 hours, so as to obtain samples for analysis, and the quantity and Z/E ratio of ajoene in each sample was determined.

The test results are shown in Table 1. As shown in the table, neutral or approximately neutral pH values of 5.5 to 8.5 are preferable. A range of pH values between 6 and 8 are most preferable.

TABLE 1

| SAMPLE NUMBER | pH | QUANTITY OF AJOENE (mg) PER 1 kg OF GARLIC | Z/E RATIO |
|---|---|---|---|
| REFERENCE EXAMPLE 1-1 | 2 | 11 | 1.7 |
| REFERENCE EXAMPLE 1-2 | 3 | 40 | 2.1 |
| REFERENCE EXAMPLE 1-3 | 4 | 112 | 3.1 |
| REFERENCE EXAMPLE 1-4 | 5 | 150 | 3.2 |

TABLE 1-continued

| SAMPLE NUMBER | pH | QUANTITY OF AJOENE (mg) PER 1 kg OF GARLIC | Z/E RATIO |
|---|---|---|---|
| EMBODIMENT 1-1 | 5.5 | 302 | 4.0 |
| EMBODIMENT 1-2 | 6 | 345 | 4.2 |
| EMBODIMENT 1-3 | 6.57 | 403 | 4.6 |
| EMBODIMENT 1-4 | 8 | 334 | 5.5 |
| EMBODIMENT 1-5 | 8.5 | 301 | 4.2 |
| REFERENCE EXAMPLE 1-5 | 9 | 51 | 2.0 |
| REFERENCE EXAMPLE 1-6 | 10 | 2 | 0.3 |

SECOND EMBODIMENT, SECOND REFERENCE EXAMPLE

INFLUENCE OF REACTION TEMPERATURE AND REACTION TIME 300 g of water was added to 1000 g of raw garlic bulbs. Subsequently, in the same way as in the first embodiment, after mashing and squeezing, about 800 g of juice was obtained. Eight 80 g specimens were drawn from the juice. In the same manner as in the first embodiment, 80 g of Panacate 810 was added to and mixed with each specimen. After mixing, the specimens were incubated at 4° C., 10° C., 20° C., 30° C., 37° C., 50° C., 55° C., 65° C., and 85° C., respectively, so as to form ajoene therein. After three hours, six hours, twelve hours, one day, two days, three days and seven days, respectively, a sample was taken from each specimen. In the same way as in the first embodiment, the quantity of ajoene in each sample was determined.

The test results are shown in Table 2. As shown in the table, the optimum incubating time period, in which the amount of ajoene reaches its maximum value, is in inverse proportion to the incubating temperature: it is at least seven days at 4° C., about six to 24 hours at 37° C., and three to 24 hours at 50° C. At incubating temperatures equal to or lower than 37° C., the amount of ajoene seldom decreases after reaching its maximum value. On the other hand, at incubating temperatures that are higher than 55° C., the rate of ajoene formation is accelerated, however, the amount of ajoene produced decreases with the period of time. When the incubating temperatures are equal to or lower than 55° C., at least 300 mg of ajoene is formed in the oil per 1 kg of raw garlic, and the Z/E ratio of the formed ajoene is at least 4. In the table, the optimum range, in which at least 300 mg of ajoene is formed per 1 kg of raw garlic, is enclosed by a bold line. Consequently, it can be appreciated that incubation temperatures equal to or lower than 50° C. especially suit the objective of the present invention.

TABLE 2

| SAMPLE NUMBER | TEMPERATURE (°C.) | QUANTITY OF AJOENE (mg) PER 1 kg OF GARLIC | | | | | | |
|---|---|---|---|---|---|---|---|---|
| | | 3 HOURS | 6 HOURS | 12 HOURS | 1 DAY | 2 DAYS | 3 DAYS | 7 DAYS |
| EMBODIMENT 2-1 | 4 | 10 | 15 | 99 | 219 | 324 | 347 | 424 |
| EMBODIMENT 2-2 | 10 | 70 | 100 | 200 | 295 | 385 | 397 | 430 |
| EMBODIMENT 2-3 | 20 | 100 | 165 | 275 | 352 | 417 | 372 | 367 |
| EMBODIMENT 2-4 | 30 | 150 | 290 | 315 | 378 | 360 | 361 | 375 |
| EMBODIMENT 2-5 | 37 | 300 | 380 | 382 | 380 | 365 | 373 | 384 |

TABLE 2-continued

| | | QUANTITY OF AJOENE (mg) PER 1 kg OF GARLIC | | | | | | |
|---|---|---|---|---|---|---|---|---|
| SAMPLE NUMBER | TEMPERATURE (°C.) | 3 HOURS | 6 HOURS | 12 HOURS | 1 DAY | 2 DAYS | 3 DAYS | 7 DAYS |
| EMBODIMENT 2-6 | 50 | 308 | 367 | 370 | 300 | 298 | 300 | 267 |
| EMBODIMENT 2-7 | 55 | 320 | 300 | 280 | 280 | 292 | 290 | 229 |
| REFERENCE EXAMPLE 2-1 | 65 | 240 | 256 | 231 | 216 | 207 | 175 | 143 |
| REFERENCE EXAMPLE 2-2 | 85 | 150 | 140 | 131 | 117 | 78 | 40 | 5 |

THIRD EMBODIMENT

INFLUENCE OF TYPE OF EDIBLE OIL 240 g of water was added to 800 g of raw garlic bulbs. Subsequently, in the same way as in the first embodiment, after mashing and squeezing, about 650 g of juice was obtained. Five 80 g specimens were drawn from the juice. 80 g of oil: Panacate 810 (Nihon Oil and Fat Co., Ltd.); refined rapeseed oil (NISSHIN OIL MILLS CO., LTD.); refined corn oil (Ajinomoto Co., Inc.); safflower oil (Ajinomoto Co., Inc.); and salad oil (NISSHIN OIL MILLS CO., LTD.) having the blend ratio 4:6 of the soybean oil and rapeseed oil were respectively added and mixed with the specimens. After mixing, the specimens were incubated at 37° C. for 24 hours. In the same way as in the first embodiment, samples were taken from each specimen and the quantity and Z/E ratio of ajoene in each sample was determined.

The test results are shown in Table 3. Even if various types of oil are used, the quantity of ajoene in the obtained samples differs only by a relatively small amount. When Panacate 810 is used, however, ajoene is most efficiently obtained.

THIRD REFERENCE EXAMPLE

From the juice obtained in the third embodiment, three 80 g specimens were taken. 80 g of solvent: ethyl alcohol; methyl alcohol; and acetone were respectively added and mixed into the specimens. After mixing, in the same way as in the third embodiment, the specimens were incubated at 37° C. for 24 hours. These ajoene-containing specimens with the organic solvents mixed therein were centrifuged at 5000 rpm for ten minutes. 2.5 g of supernatant was then taken from the specimens, and the volume of the liquid samples was adjusted to 25 ml by adding dichloromethane to the samples. In the same way as in the first embodiment, the quantity and Z/E ratio of ajoene in each sample was determined.

The test results are shown in Table 3. As shown in the table, when oil is used, a larger amount of ajoene is obtained as compared with when organic solvents are used. Furthermore, Z-ajoene occupies a larger ratio.

TABLE 3

| SAMPLE NUMBER | TYPE OF OIL AND FAT . SOLVENT | QUANTITY OF AJOENE (mg) PER 1 kg OF GARLIC | Z/E RATIO |
|---|---|---|---|
| EMBODIMENT 3-1 | PANACATE 810 | 404 | 4.7 |
| EMBODIMENT 3-2 | REFINED RAPESEED OIL | 308 | 4.4 |
| EMBODIMENT 3-3 | REFINED CORN OIL | 328 | 4.0 |
| EMBODIMENT 3-4 | REFINED SAFFLOWER OIL | 327 | 4.1 |
| EMBODIMENT 3-5 | SALAD OIL | 303 | 5.5 |
| REFERENCE EXAMPLE 3-1 | ETHYL ALCOHOL | 10 | 1.7 |
| REFERENCE EXAMPLE 3-2 | METHYL ALCOHOL | 7 | 1.2 |
| REFERENCE EXAMPLE 3-3 | ACETONE | 14 | 1.1 |

FOURTH EMBODIMENT, FOURTH REFERENCE EXAMPLE

SURVEY ON THE AMOUNT OF WATER TO BE ADDED TO GARLIC 0 part, 25 parts, 50 parts, 75 parts, 100 parts and 200 parts by weight of water were respectively added to six 100 g parts of raw garlic bulbs. After mashing and squeezing, juice was obtained in the same way as in the first embodiment, and the volume of juice was measured. From each volume of juice, a 50 g sample was taken, and 50 g of Panacate 810 was added to the sample. After mixing the samples in the same way as in the first embodiment, the mixture was incubated at 37° C. for 24 hours, and the quantity and Z/E ratio of ajoene in each sample was determined.

The test results are shown in Table 4. When the amount of water added to the raw garlic is in the range between 0% and 200% by weight, the water has no large influence on the formation of ajoene. Considering that, when the mixed amount of oil is increased as the volume of juice is increased, the concentration of obtained ajoene is decreased, it is clear that the addition of a large amount of water is not economical. Therefore, it is suitable that only 0 to 100% by weight of water is added to the garlic.

TABLE 4

| SAMPLE NUMBER | AMOUNT OF ADDED WATER (% BY WEIGHT) | QUANTITY OF AJOENE (mg) PER 1 kg OF GARLIC | CONCENTRATION OF AJOENE (µg per 1 g of oil) | Z/E RATIO |
| --- | --- | --- | --- | --- |
| EMBODIMENT 4-1 | 0 | 311 | 1,013 | 4.3 |
| EMBODIMENT 4-2 | 25 | 383 | 728 | 4.8 |
| EMBODIMENT 4-3 | 50 | 355 | 511 | 5.1 |
| EMBODIMENT 4-4 | 75 | 366 | 300 | 4.7 |
| EMBODIMENT 4-5 | 100 | 320 | 272 | 4.5 |
| REFERENCE EXAMPLE 4-1 | 200 | 294 | 152 | 4.2 |

FIFTH EMBODIMENT, FIFTH REFERENCE EXAMPLE

SURVEY ON THE AMOUNT OF EDIBLE OIL TO BE ADDED TO JUICE 120 g of water was added to 400 g of the raw garlic bulbs. After mashing and squeezing in the same way as in the first embodiment, a little over 320 g of juice was obtained. From the juice, samples of 80 g each were taken, and 50%, 100%, 200% and 400% by weight of Panacate 810 were added, respectively, to the samples. In the same way as in the first embodiment, the samples were mixed and incubated at 37° C. for 24 hours, and the quantity and Z/E ratio of ajoene in each sample was determined.

The test results are shown in Table 5. As shown in the table, when the amount of oil added to juice is in the range between 50% and 400% by weight, there is no large influence on the total quantity of obtained ajoene. However, to prepare edible oil containing a large amount of ajoene, increasing the quantity of oil is not-economical. It is therefore preferable that about 50% to 200% by weight of oil is added to and mixed with the garlic juice.

SIXTH EMBODIMENT, SIXTH REFERENCE EXAMPLE

INFLUENCE OF THE PROCESS STEP OF JUICING

To obtain sample EMBODIMENT 6-1, 100 g of raw garlic was mashed, 100 g of Panacate 810 was added to the mashed garlic, and the sample was mixed and incubated at 37° C. for 24 hours. To obtain sample EMBODIMENT 6-2, 30 g of water was added to 100 g of the same variety of garlic. After mashing and squeezing, 80 g of juice was obtained. Subsequently, 80 g of Panacate 810 was added to the juice. After mixing, the sample was incubated at 37° C. for 24 hours. To obtain sample REFERENCE EXAMPLE 6-1, 100 g of raw garlic, 30 g of water and 80 g of Panacate 810 were mixed, mashed and incubated at 37° C. for 24 hours. The quantity and Z/E ratio of ajoene in each sample was determined in the same way as in the first embodiment.

The test results are shown in table 6. Ajoene can be obtained by any of the aforementioned sixth embodiments and reference example. When garlic juice is used, a higher yield of ajoene is obtained as compared with when mashed garlic is used. In REFERENCE EXAMPLE 6-1, in which a mixture of garlic and oil was mashed, a smaller amount of ajoene was obtained. Consequently, it is preferable that the garlic is mixed with oil after mashing the garlic, and it is especially preferable that the juice is mixed with oil after squeezing juice from the mashed garlic.

TABLE 6

| SAMPLE NUMBER | QUANTITY OF AJOENE (mg) PER 1 kg OF GARLIC | Z/E RATIO |
| --- | --- | --- |
| EMBODIMENT 6-1 | 328 | 4.1 |
| EMBODIMENT 6-2 | 412 | 4.7 |
| REFERENCE EXAMPLE 6-1 | 210 | 3.1 |

TABLE 5

| SAMPLE NUMBER | AMOUNT OF OIL AND FAT (% BY WEIGHT) | QUANTITY OF AJOENE (mg) PER 1 kg OF GARLIC | CONCENTRATION OF AJOENE (µg per 1 g of oil) | Z/E RATIO |
| --- | --- | --- | --- | --- |
| EMBODIMENT 5-1 | 50 | 375 | 938 | 4.2 |
| EMBODIMENT 5-2 | 100 | 401 | 501 | 5.1 |
| EMBODIMENT 5-3 | 200 | 382 | 239 | 4.4 |
| REFERENCE EXAMPLE 5-1 | 400 | 355 | 111 | 4.0 |

As aforementioned, it is expected that ajoene, especially Z-ajoene obtained in the method of processing garlic according to this invention, will effectively inhibit the platelet aggregation, will be an effective antibacterial and antifungal agent and will provide other various pharmacological effects. Moreover, if suitable conditions are selected, at least 300 mg of ajoene can be formed from 1 kg of raw garlic bulbs. When the Z/E ratio is over 4, ajoene products that are suitable for use in foods or drugs. Furthermore, according to the invention, ajoene-containing edible oil, especially oil containing a relatively large quantity of Z-ajoene is efficiently obtained.

What is claimed is:

1. A method of preparing ajoene-containing oil, comprising the steps of:

(a) adding water to raw garlic bulbs;

(b) mashing the garlic bulbs;

(c) squeezing juice from the mashed garlic bulbs;

(d) adding edible oil to the garlic juice;

(e) mixing the edible oil and the garlic juice; and (f) incubating the mixture at a temperature ranging between 0° C. and 55° C. for a period of between three hours and seven days thereby forming ajoene-containing oil; wherein step (f) further comprises the step of forming not less than 300 mg of ajoene per 1 kg of raw garlic bulbs.

2. The method of preparing ajoene-containing oil according to claim 1 further comprising the step of separating oil phase from the mixture of the garlic juice and the edible oil.

3. The method of preparing ajoene-containing oil according to claim 1 wherein step (d) comprises the step of adding 50 to 200 parts by weight of the edible oil to 100 parts by weight of the garlic juice.

4. The method of preparing ajoene-containing oil according to claim 1 wherein step (f) further comprises the step of forming ajoene having a Z-ajoene/E-ajoene ratio of at least 4.

5. The method of preparing ajoene-containing oil according to claim 1 further comprising the step of selecting a medium-chain fatty acid triglyceride as the edible oil.

* * * * *